(12) United States Patent
Althoff et al.

(10) Patent No.: US 8,506,294 B2
(45) Date of Patent: Aug. 13, 2013

(54) DEVICE FOR PRODUCING DENTAL WORKPIECES

(75) Inventors: Olaf Althoff, Wessling (DE); Daniel Suttor, Seefeld (DE); Stefan Hoescheler, Herrsching (DE); Martin Beuschel, Munich (DE)

(73) Assignee: 3M Innovative Properties Company, St. Paul, MN (US)

( * ) Notice: Subject to any disclaimer, the term of this patent is extended or adjusted under 35 U.S.C. 154(b) by 368 days.

(21) Appl. No.: 10/326,274

(22) Filed: Dec. 23, 2002

(65) Prior Publication Data

US 2003/0132539 A1 Jul. 17, 2003

Related U.S. Application Data

(63) Continuation of application No. PCT/EP01/07050, filed on Jun. 22, 2001.

(30) Foreign Application Priority Data

Aug. 1, 2000 (DE) .................................. 100 37 531
Jun. 22, 2002 (DE) .............................. 200 10 643 U

(51) Int. Cl.
*A61C 3/00* (2006.01)
*A61C 13/38* (2006.01)

(52) U.S. Cl.
USPC ........................................ 433/163; 433/223

(58) Field of Classification Search
USPC ................. 433/49, 50, 163, 223; 269/16, 89, 269/909, 287; 264/19; 206/63.5, 368, 388; 425/542; 29/896.1, 896.11, 281.1
See application file for complete search history.

(56) References Cited

U.S. PATENT DOCUMENTS

| | | | |
|---|---|---|---|
| 4,615,678 A | 10/1986 | Moermann et al. | |
| 5,490,810 A * | 2/1996 | Hahn et al. | 451/165 |
| 5,813,859 A * | 9/1998 | Hajjar et al. | 433/223 |
| 6,190,171 B1 * | 2/2001 | Hajjar et al. | 433/218 |
| 6,454,568 B1 * | 9/2002 | Beuschel et al. | 433/163 |
| 6,495,073 B2 * | 12/2002 | Bodenmiller et al. | 264/16 |
| 7,077,391 B2 * | 7/2006 | Filser et al. | 269/287 |

FOREIGN PATENT DOCUMENTS

| | | |
|---|---|---|
| CA | 2 280 352 A1 | 2/2000 |
| DE | 29815486 U1 | 2/2000 |
| DE | 44 36 231 B4 | 1/2006 |
| EP | 0 391446 A | 10/1990 |
| EP | 0391446 | 10/1990 |
| EP | 0759728 | 10/1997 |

(Continued)

OTHER PUBLICATIONS

English translation of EP0982009, Mar. 1, 2000.*

*Primary Examiner* — Todd Manahan
*Assistant Examiner* — Michael R Ballinger
(74) *Attorney, Agent, or Firm* — X. Christina Huang

(57) ABSTRACT

The invention relates to a device for the automated production of dental workpieces. A blank is inserted in a substantially slab-shaped support of the device, said support being dimensioned such that the blank does not extend beyond it in any direction. The blank is linked with corresponding inner walls of a recess provided in the support only on two opposite faces while a gap is left between the other inner walls of the recess and the corresponding faces of the blank. The inventive design allows to avoid tensions and microcracks of the blank material thereby caused. The gaps further make the blank directly accessible for a lateral working by the milling tool.

10 Claims, 3 Drawing Sheets

(56) References Cited

FOREIGN PATENT DOCUMENTS

| | | |
|---|---|---|
| EP | 0982009 | 3/2000 |
| JP | 10 192305 A | 7/1998 |
| JP | 2000 107202 A | 4/2000 |
| WO | WO 95/30382 A1 | 11/1995 |

* cited by examiner

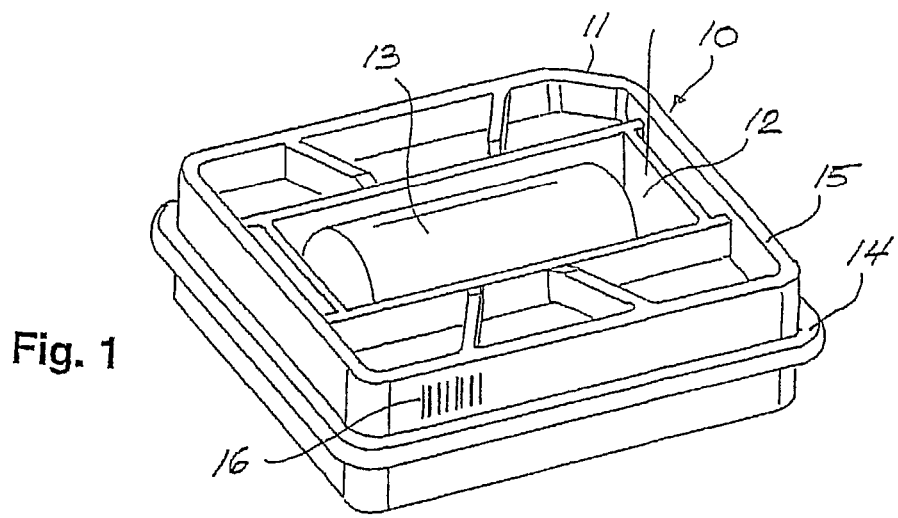
Fig. 1
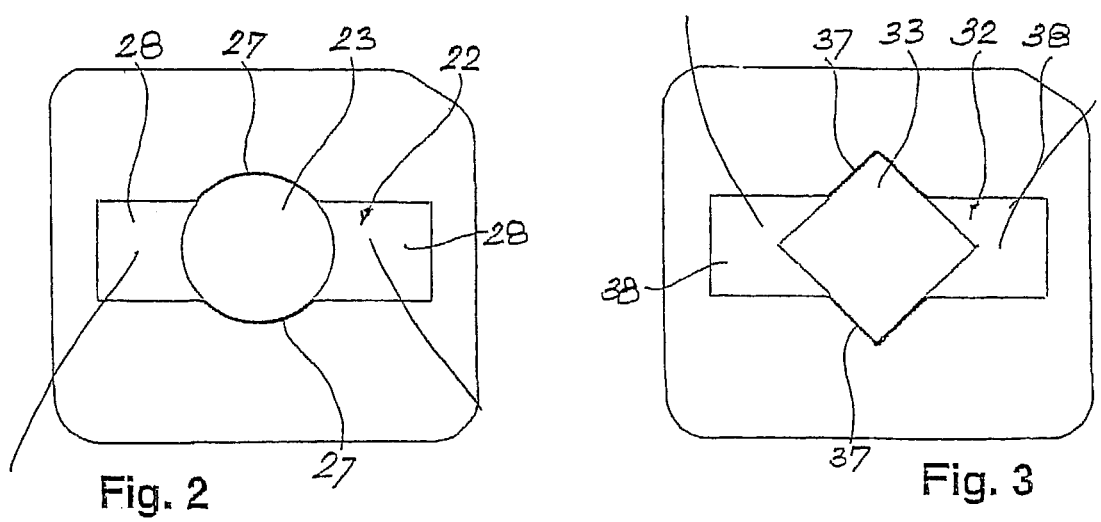
Fig. 2
Fig. 3
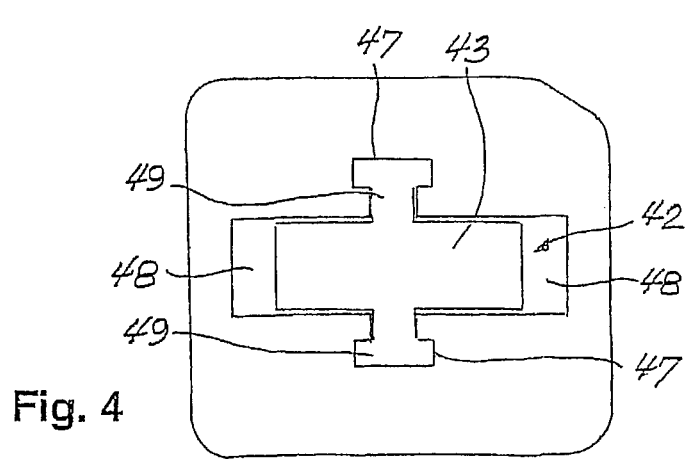
Fig. 4

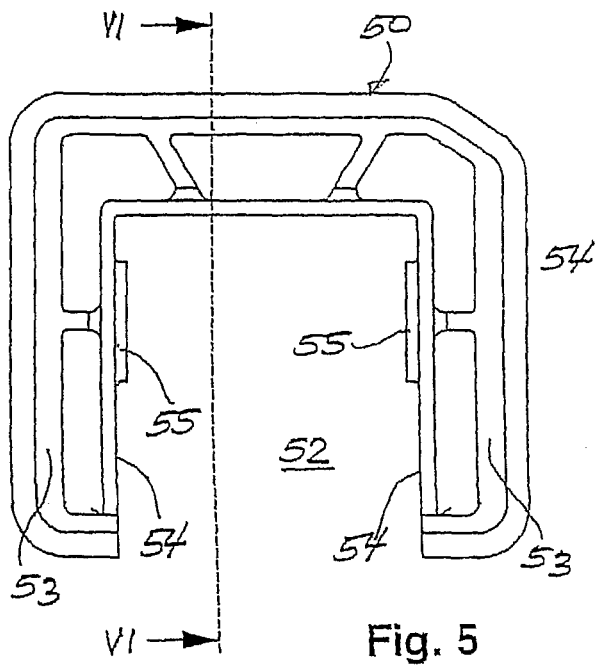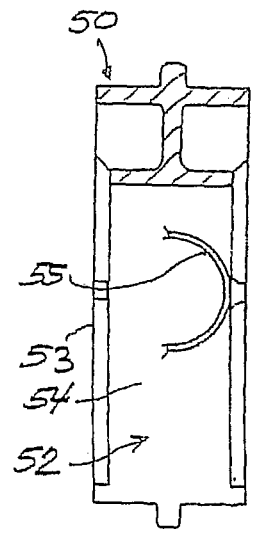
Fig. 5  Fig. 6
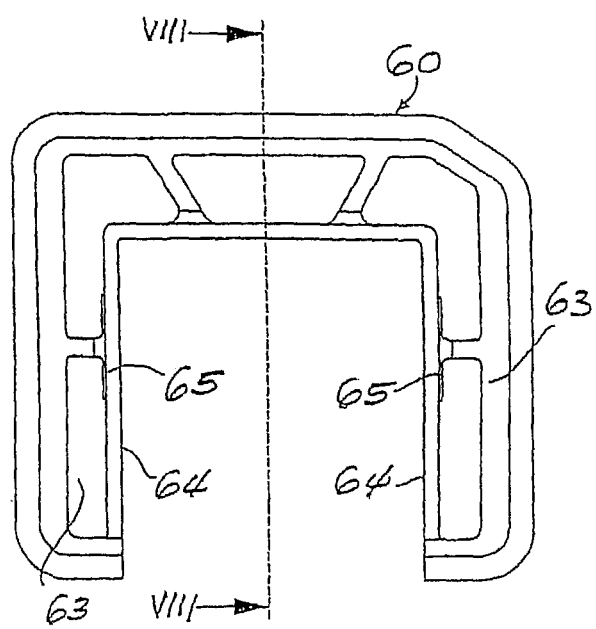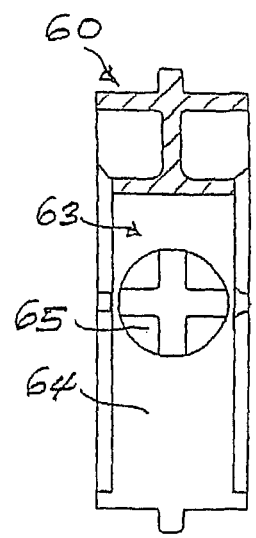
Fig. 7  Fig. 8

DEVICE FOR PRODUCING DENTAL WORKPIECES

CROSS-REFERENCE TO RELATED APPLICATION

This application is a continuation of PCT Application No. PCT/EP01/07050 filed Jun. 22, 2000,claims priority to German Application No. 200 10 643.0 filed Jun. 22, 2002, and claims priority to German Application No. 100 37 531.6 filed Aug. 1, 2000.

BACKGROUND AND SUMMARY OF THE INVENTION

Tooth replacement parts, such as crowns, bridges or implants, and other dental workpieces are normally produced by the desired shape of the workpiece being optically or mechanically scanned from a corresponding model, and by the data thus obtained being used to generate milling tracks. Based on these milling tracks, the dental workpiece is then produced from a blank in a milling tool or other suitable machine tool.

EP 0 759 728 B1 discloses a device in which the blank intended for production of a dental prosthesis is embedded in a ring of metal, ceramic or hard plastic. For cost reasons, the blank is dimensioned so that as little as possible of the expensive material of the blank is wasted during the machining. The generally cylindrical blank is embedded in the ring by means of a dental adhesive applied all around it and, together with the ring, it is inserted into a support body which in turn is clamped into the machine tool.

Particularly in the case of fairly large blanks for production of bridges, it has been found that adhesive applied on all sides leads to stress cracks during milling, which stress cracks are not easily discernible in the blank. These cracks can run through the entire blank, transverse to the longitudinal axis, and can thus make the workpiece unusable.

The effect becomes apparent when, after milling of the top side, the underside is exposed and these two planes meet one another. Since the strength of the material normally used is only about 20 to 30 MPa in the raw state, and since that of the epoxy adhesives generally used lies in the same range, a blank which is surrounded all round by adhesive is subjected to forces in a biaxial stress field, which forces can amount to several 100 N depending on the adhesive surface. The notch effects which occur during milling intensify this effect, with the result that the strength of the material of the blank is exceeded and the latter fractures transverse to the longitudinal direction.

A further difficulty in the known device is that, in the case of adhesive-bonding, the adhesive inevitably runs on the mutually parallel cylinder faces of blank and ring and reaches those surface parts of the blank which are to be machined, and thus also reaches the milling head. As a result of this, the milling head is soiled, and the precision of the milling is adversely affected.

These difficulties also exist in the device which is known from DE 298 15 486 U1, in that the blank in said document is inserted into the central opening of the plate-shaped support body with adhesive applied all around it.

An object of the invention is to make available a device for producing dental workpieces which permits better machining of the blank.

The solution to this object is a device for producing dental workpieces, comprising a blank, and a support body with a recess formed with support body recess surfaces at least partially surrounding the blank and with support body clamping surfaces engageable in use with clamping surfaces of a machine tool, wherein said blank is connected to the support body along only a portion of the support body recess surfaces. The described stresses and microcracks are largely avoided by means of the blank and the support body being only partially connected to each other. Surprisingly, it has been found that the fractures mentioned above occur only in a biaxial stress field which is present in the case of an all-round adhesive-bonding.

The gap, provided for in certain preferred embodiments by arranging the blank at a distance from the support body at locations not connected to the support body, between the blank and the recess in the support body surrounding it has the advantage that the blank can be approached laterally by the tool-piece of the machine tool. The milling head can immediately begin its work in this gap, without first having to drill into the material, as is the case in the prior art. Since drilling work subjects the milling cutter to excessive stresses and wear, the service life of the milling cutter is substantially increased by this arrangement. Furthermore, the milling operation is finished more quickly, because slow movements of immersion into the material of the blank are avoided or at least reduced.

Certain preferred embodiments of the invention improve the free lateral accessibility of the blank by providing one or more of the original following features:

(i) An arrangement wherein the blank is connected on two opposite sides to the support body;
(ii) An arrangement wherein the support body is of generally U-shaped design and the blank is connected to branches of the U-shape;
(iii) An arrangement wherein holders for receiving opposite ends of the blank are integrally formed onto the branches of the support body;
(iv) An arrangement wherein the holders are designed as projections on the inner walls or as depressions in inner walls of the branches; and
(v) An arrangement wherein the recess has widened areas, which lie opposite one another and with which the blank is connected, and wherein the recess has further areas arranged at a distance from the blank.

In accordance with certain embodiments, the connection between blank and support body can consist of an embedding, an adhesive-bonding, or an interlocking mechanical holding arrangement. In the case of the adhesive-bonding, curving or beveling of the blank surfaces at the transition of the exposed side surface is advantageous because it largely eliminates the possibility of the tool becoming soiled by the adhesive.

In addition to the above embodiments in which the connection between blank and support body is realized for example by means of an embedding, an adhesive-bonding or an interlocking mechanical holding arrangement, the subject of the present application also includes, embodiments for example in which the blank is connected to the support body by means of at least one further body being arranged between blank and support body, which further body is connected to the blank and also to the support body. This at least one further body can be connected to the blank or to the support body for example by an embedding, an adhesive-bonding or an interlocking mechanical holding arrangement. A preferred embodiment consists of the adhesive-bonding of the blank to the at least one further body on the one hand, and the adhesive-bonding of the at least one further body to the support body on the other hand.

The material from which the at least one further body is made can be selected essentially freely, and it can be adapted to the requirements of the overall arrangement. For example, it is possible for the at least one further body to be made from the material of the blank or from the material of the support body. Likewise, the at least one further body can be produced from two or more materials and can for example be built up in layers.

If the blank is connected to the support body via two or more further bodies, the two or more further bodies can be the same as or different than one another, in which case the differences can lie for example in the geometry and/or the materials from which the at least two further bodies are made.

In order to create a connection, it is likewise possible first to connect the blank to a first further body, which is connected in turn to a second further body, the latter being connected to the support body. According to this embodiment, it is of course also possible for three or more further bodies to serve as a connection between blank and support body, in which case the connections between the further bodies and the connection between one of the further bodies and the blank or the support body can be the same as or different than one another, and can for example represent an embedding, an adhesive-bonding or an interlocking mechanical holding arrangement.

An embodiment is preferred, among others, in which the blank is connected on two opposite sides to a further body in each case, each of the further bodies being connected to the support body via its side lying opposite the point of connection to the blank. An embodiment is further preferred in which these two further bodies are made from the material of the support body. The two further bodies are particularly preferably connected to the blank by adhesive bonding.

The feature of dimensioning the support body and the blank so that the blank does not extend beyond the support body in any direction affords effective protection of the blank against mechanical influences. Since the support body alone determines the outer shape of the unit formed by the blank and the support body, it can be configured without limitation so that it can be stacked together with further units, irrespective of the exact shape of the blank, and permits automatic loading, removal and turning in the course of automatic production.

In the development of preferred embodiments of the invention, the support body provides enough space for application of a code, in which case the machine tool can be controlled so that, on the basis of the scanned code, it automatically executes the correct machining operation with the correct tool-piece for the blank contained in the support body, for example follows the generated milling tracks or, if there is insufficient correspondence, it suppresses the machining operation.

In accordance with certain preferred embodiments, the code can be changed or even removed by the machine tool, for example by the milling cutter. The advantage of this is that unintentional twofold machining of the same blank is avoided. At the same time, it is possible to ensure that only original blanks, as supplied by the manufacturer, and support bodies can be machined, whereas used support bodies re-fitted with blanks are rejected.

The plate shape of the support body, with large parallel surfaces perpendicular to the recess surfaces connected with the blank, is particularly favorable for automatic handling and stacking, for example in the context of storage in magazines.

The development of embodiments of the invention with the shape of the outside of the support body being asymmetrical ensures proper orientation of the support body and blank in the machine tool.

The feature of certain embodiments with an injection molded plastic support body is of interest from the point of view of the cost of material and cost of production of the support body.

Certain particular preferred embodiments of the invention include a device for producing dental workpieces with a blank and with a support body, in which
(a) the support body has a recess at least partially surrounding the blank,
(b) the support body can be clamped via its outside into a machine tool,
(c) the blank is connected on two opposite sides to the support body,
(d) the connection between the support body and the blank consists of an adhesive-bonding,
(e) the support body is dimensioned so that the blank does not extend beyond the support body in any direction;
(f) the support body carries a code which relates to the blank,
(g) the code can be changed by the machine tool,
(h) the support body has substantially the shape of a plate whose parallel large surfaces are perpendicular to the surfaces connected to the blank, and
(i) the support body is a plastic injection-molded part.

Certain particular preferred embodiments of the invention include a device for producing dental workpieces with a blank and with a support body, in which
(a) the support body has a recess at least partially surrounding the blank,
(b) the support body can be clamped via its outside into a machine tool,
(c) the blank is connected on two opposite sides to the support body,
(d) the connection between the support body and the blank is realized by means of a further body being arranged on each of two opposite sides of the blank, which further body is connected to the blank and also to the support body,
(e) the connections between the support body and the further bodies and between the blank and the further bodies consist in each case of an adhesive-bonding,
(f) the support body is dimensioned so that the blank does not extend beyond the support body in any direction;
(g) the support body carries a code which relates to the blank,
(h) the code can be changed by the machine tool,
(i) the support body has substantially the shape of a plate whose parallel large surfaces are perpendicular to the surfaces connected to the blank, and
(k) the support body is a plastic injection-molded part.

Other objects, advantages and novel features of the present invention will become apparent from the following detailed description of the invention when considered in conjunction with the accompanying drawings.

BRIEF DESCRIPTION OF THE DRAWINGS

FIG. 1 shows a plan view of a support body;
FIGS. 2-4 show variants of the support body from FIG. 1 in diagrammatic views;
FIG. 5 shows a plan view of a support body according to another illustrative embodiment;
FIG. 6 shows a cross section through the support body along the line VI-VI in FIG. 5;
FIG. 7 shows a plan view of a variant of the support body from FIG. 5;

FIG. 8 shows a cross section through the support body along the line VIII-VIII in FIG. 7;

DETAILED DESCRIPTION OF THE DRAWINGS

Figure 9:
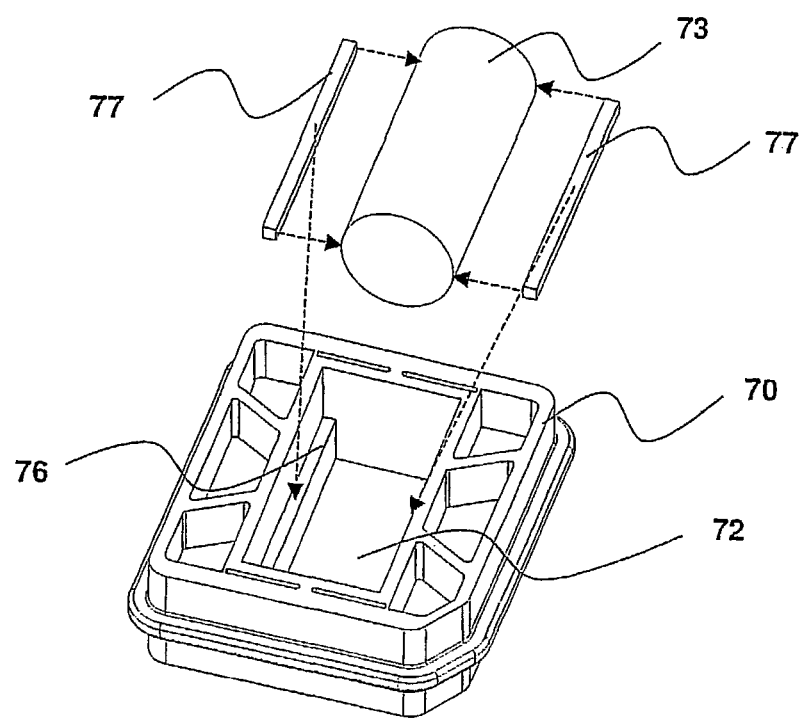
FIG. 9 shows a plan view of a support body according to another illustrative embodiment; and The support body 10 shown in FIG. 1, and produced as a plastic injection-molded part, is basically plate-shaped with plane-parallel rectangular faces with a lower height in relation to their sides. A corner area 11 is beveled so as to be able to determine the orientation of the support body 10.

A central rectangular recess 12 serves to receive a blank 13 for dental workpieces which is cylindrical in this illustrative embodiment. On two opposite surfaces, the blank 13 is adhesively bonded to the corresponding walls of the recess 12.

Between the two other walls of the recess 12 and those faces of the blank 13 which face them, there is a gap into which the milling head can be introduced at the start of the machining operation.

On its outside, the support body 10 is provided with a peripheral bead 14 which serves for inserting it into guide grooves of the machine tool.

The greatest thickness of the support body 10 is in the area of its outer peripheral wall 15. This thickness is dimensioned so that it extends above the blank 13 in such a way that the latter is protected in all directions against mechanical damage.

The peripheral wall 15 carries a barcode 16 which can be printed on directly or can be printed onto a stick-on strip or can be formed directly into the material of the support body 10. The barcode 16 serves to identify the material, dimensions and/or other properties of the blank 13 contained in the support body 10.

In the illustrative embodiment according to FIG. 1, the surfaces of the blank 13 adhesively bonded to the walls of the recess 12 are cylindrical. This means that the adhesive cannot reach or cannot readily reach those surfaces which are to be machined by the milling head. The same effect is achieved if the adhesive surfaces of the blank are plane and are beveled at the transition to the upwardly and downwardly exposed surfaces. The defined rectangular connection zones which are obtained in this configuration are advantageous for reducing the stress cracks which were mentioned in the introduction.

Instead of the purely rectangular configuration shown in FIG. 1, the recess can also have one of the shapes shown in FIGS. 2 through 4. In these cases, the mutually opposite longer faces of the recess 22, 32, 42 each have a widened area 27, 37, 47 in which the blank 23, 33, 43 is secured. In the other areas 28, 38, 48 of the recess 22, 32, 42, the blank 23, 33, 43 lies at a corresponding distance from the walls of the respective recess 22, 32, 42 and is therefore readily accessible for the machine tool.

The configurations according to FIGS. 2 through 4 are also suitable for an adhesive-free holding arrangement, for example by mechanical interlocking. This is particularly good in the configuration according to FIG. 4 in which the blank 43 has, on two opposite faces, mushroom-shaped attachments 49 for engagement in the matching widened areas 47 of the recess 42.

In the illustrative embodiment according to FIGS. 5 and 6, the support body 50 is of U-shaped design, so that, on one side, the recess 52 is open toward the outside. The blank (not shown) which in this case is assumed to be cylindrical is secured, for example adhesively bonded, between the branches 53 of the U-shape. For positioning and additional holding, approximately semicylindrical ridges 55 are provided on the inner walls 54 of the branches 53, and the blank is fitted into these ridges 55.

Despite the substantially rigid nature of the support body 50, the illustrated U-shape gives it a certain amount of flexibility which is favorable both for insertion and removal of the support body and also for avoiding undesired stresses on the blank.

If, because of the U-shape, the peripheral wall on the front surface delivered to the machine tool has no room for a coding, the latter can be provided on a separate support strip (not shown) which is arranged on the support body 50 and spans the open side of the U-shape, without altering the mechanical properties or other properties of the support body 50.

The variant according to FIGS. 7 and 8 differs from the design according to FIGS. 5 and 6 in that the front ends of the blank (not shown), which is again assumed to be cylindrical, engage in circular depressions 65 which are provided in the inner walls 64 of the branches 63 of the support body 60, which is otherwise of the same configuration. In this case, the blank can be securely and accurately positioned in the support body 60 without adhesive, and without any other connection means, that is to say exclusively by the interlocking engagement of its ends in the depressions 65.

The variant according to FIG. 9 shows a support body 70 which has a recess 72 with steps 76 on two opposite side walls. The two further bodies 77 shaped as square bars are secured with their underside on the upper edge of the steps 76, and these two further bodies 77 are in turn each secured via a side edge to two opposite side surfaces of the blank 73. In this embodiment, adhesive-bonding of the further bodies 77 to the blank 73 is preferred, and also adhesive-bonding of the lower edges of the further bodies 77 to the upper edges of the steps 76 of the side walls of the recess 72.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A system comprising: a substantially cylindrical dental blank having axially opposite ends and a device for mounting the substantially cylindrical dental blank comprising:
   a support body separate from, and clampable into, a machine tool, the support body defining a recess formed with support body recess surfaces that at least partially surround the dental blank, the support body further defining support body clamping surfaces clampable into the machine tool using clamping surfaces of the machine tool,
   wherein each of the two axially opposite ends of the dental blank is adhesively bonded to the support body via a holder on the corresponding support body recess surface;
   wherein a gap is provided between the support body and the dental blank, wherein the gap is of sufficient size to allow a milling head to work on the dental blank between the support body and the dental blank.

2. The system as claimed in claim 1, wherein the device further comprising a peripheral bead, and wherein the device clamping surfaces face outwardly of said support body.

3. The system as claimed in claim 1, wherein each holder is integrally formed onto the corresponding support body recess surface.

4. The system as claimed in claim 3, wherein the each holder is designed as a projection on the corresponding support body recess surface or as a depression on the corresponding support body recess surface.

5. The system as claimed in claim 1, wherein the support body is dimensioned so that the blank does not extend beyond the support body in any direction.

6. The system as claimed in claim 1, wherein the support body carries a code which relates to the blank.

7. The system as claimed in claim 6, wherein the code can be changed by the machine tool.

8. The system as claimed in claim 1, wherein the outside of the support body is shaped so as to be asymmetrical.

9. The system as claimed in claim 1, wherein the recess has a substantially rectangular shape.

10. The system as claimed in claim 1, wherein the support body has a U-shaped design.

* * * * *

UNITED STATES PATENT AND TRADEMARK OFFICE
CERTIFICATE OF CORRECTION

PATENT NO. : 8,506,294 B2
APPLICATION NO. : 10/326274
DATED : August 13, 2013
INVENTOR(S) : Olaf Althoff et al.

It is certified that error appears in the above-identified patent and that said Letters Patent is hereby corrected as shown below:

On the Title Page, Item (30)
Column 1 (Foreign Application Priority Data); Line 2, Delete "2002" and insert -- 2000 --, therefor.
Column 1 (Foreign Application Priority Data); Line 2, Delete "200 10 643 U" and insert -- 200 10 643 --, therefor.

In the Specification
Column 1
Line 8; Delete "2000," and insert -- 2001, --, therefor.
Line 9; Delete "2002," and insert -- 2000, --, therefor.

Signed and Sealed this
Thirty-first Day of December, 2013

Margaret A. Focarino
*Commissioner for Patents of the United States Patent and Trademark Office*